United States Patent
Okunishi et al.

(10) Patent No.: US 11,033,473 B2
(45) Date of Patent: Jun. 15, 2021

(54) HAIR RESTORATION/GROWTH STIMULATING AGENT

(71) Applicant: Kinjirushi Co., Ltd., Aichi (JP)

(72) Inventors: Isao Okunishi, Aichi (JP); Tomoe Kato, Aichi (JP)

(73) Assignee: KINJIRUSHI CO., LTD., Nagoya (JP)

( * ) Notice: Subject to any disclaimer, the term of this patent is extended or adjusted under 35 U.S.C. 154(b) by 0 days.

(21) Appl. No.: 16/721,332

(22) Filed: Dec. 19, 2019

(65) Prior Publication Data

US 2020/0108005 A1  Apr. 9, 2020

Related U.S. Application Data

(63) Continuation of application No. 15/737,097, filed as application No. PCT/JP2016/085968 on Dec. 2, 2016, now abandoned.

(30) Foreign Application Priority Data

Dec. 2, 2015 (JP) .................................. 2015-235965

(51) Int. Cl.
| | | |
|---|---|---|
| A61K 8/49 | (2006.01) | |
| A61Q 7/00 | (2006.01) | |
| A61K 31/7048 | (2006.01) | |
| A61K 8/60 | (2006.01) | |
| A61K 31/353 | (2006.01) | |
| A61K 36/31 | (2006.01) | |
| A61K 8/9789 | (2017.01) | |
| A61K 8/365 | (2006.01) | |
| A61K 8/37 | (2006.01) | |
| A23L 33/105 | (2016.01) | |

(52) U.S. Cl.
CPC ............ *A61K 8/4973* (2013.01); *A61K 8/365* (2013.01); *A61K 8/37* (2013.01); *A61K 8/49* (2013.01); *A61K 8/60* (2013.01); *A61K 8/9789* (2017.08); *A61K 31/353* (2013.01); *A61K 31/7048* (2013.01); *A61K 36/31* (2013.01); *A61Q 7/00* (2013.01); *A23L 33/105* (2016.08)

(58) Field of Classification Search
CPC .... A31K 8/4973; A61K 8/9789; A61K 8/365; A61K 8/37; A61K 8/49; A61K 8/60; A61K 31/353; A61K 31/7048; A61K 36/31; A61Q 7/00; A23L 33/105; A61P 17/14
See application file for complete search history.

(56) References Cited

U.S. PATENT DOCUMENTS

| | | |
|---|---|---|
| 5,124,354 A | 6/1992 | Green |
| 5,338,838 A | 8/1994 | Hagiwara et al. |
| 2015/0342850 A1 | 12/2015 | Combs et al. |

FOREIGN PATENT DOCUMENTS

| | | |
|---|---|---|
| CN | 103857379 A | 6/2014 |
| EP | 1430933 A2 | 6/2004 |
| JP | S59-184116 A | 10/1984 |
| JP | S62215516 A | 9/1987 |
| JP | H0363213 A | 3/1991 |
| JP | H06-329519 A | 11/1994 |
| JP | 2000-154123 A | 6/2000 |
| JP | 2007137794 A | 6/2007 |
| JP | 2008239545 A | 10/2008 |
| JP | 2008260747 A | 10/2008 |
| JP | 2000297015 A | 10/2014 |
| JP | 2014528448 A | 10/2014 |
| KR | 20120039384 A | 6/2014 |
| WO | 2011058661 A1 | 3/2013 |
| WO | 2013/052545 A1 | 4/2013 |
| WO | 2014095289 A2 | 6/2014 |

OTHER PUBLICATIONS

Office Action issued in the counterpart Taiwanese Application No. 105139975 dated May 28, 2020 and English translation.

(Continued)

*Primary Examiner* — John Mabry
(74) *Attorney, Agent, or Firm* — Westman, Champlin & Koehler, P.A.; Z. Peter Sawicki; Amanda M. Prose

(57) ABSTRACT

Provided is a hair restoration/growth stimulating agent containing at least one type of flavonoid represented by formula (I) as an active ingredient. Further provided is a hair restoration/growth stimulating agent containing at least one type of phenylpropanoid represented by formula (II) as an active ingredient.

[Formula 1]

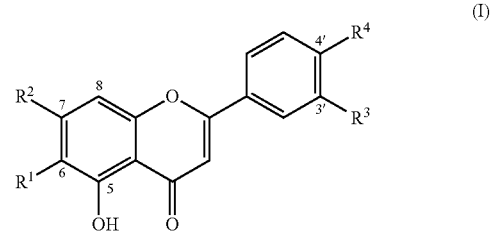

(I)

[Formula 2]

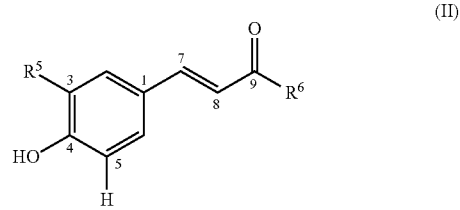

(II)

18 Claims, 10 Drawing Sheets

Specification includes a Sequence Listing.

(56) References Cited

OTHER PUBLICATIONS

Office Action in the counterpart Chinese Application No. 201680034927.4 dated Oct. 14, 2020 and its English translation.
International Search Report for Application No. PCT/JP2016/085968, dated Mar. 7, 2017.
Written Opinion of the International Searching Authority for Application No. PCT/JP2016/085968, dated Mar. 7, 2017.
Nagai, Masashi et al. (2010) "The effect of isosaponarin isolated from wasabi leaf on collagen synthesis in human fibroblasts and its underlying mechanism" J Nat Med 64:305-312.
Takeoka, Atshushi et al. (2012) "WASABI's functional molecule and the efficacy", Fragrance Journal, vol. 40, No. 4, pp. 11-16; English Abstract.
Yoshida, Shuhei et al. (2014) "Component Analysis of Wasabi Leaves and an Evaluation of their Anti-inflammatory Activity" Food Science and Technology Research, 21 (2), 247-253, 2015.
Decision of Refusal in corresponding Japanese Patent Application No. 2017-554213, dated Sep. 17, 2019.
Hosoya, T., et al. "Five novel flavonoids from Wasabia japonica." Tetrahedron. (2005), vol. 61, pp. 7037-7044.
Sultana, T., et al. "Comparison of flavour compounds in wasabi and horseradish." Food, Agriculture & Environment. (2003), vol. 1, Issue 2, pp. 117-121.
"Dosage Forms/Routes of Administration." (Oct. 14, 2010). Accessed Jul. 5, 2018. Available from: <https://www.pharmacy-tech-study.com/dosage-forms.html>.
Office Action issued in corresponding Japanese patent application No. 2017-554213, dated Jan. 31, 2019; and machine English translation.
Partial supplementary European search report issued in related European patent application No. 16870840.2 dated Feb. 11, 2019.
Notice of Preliminary Rejection arid its English translation issued in related Korean patent application No. 10-2017-7035903 dated Mar. 22. 2019.
Extended European Search Report issued for EP 16870840.2, dated May 20, 2019.
PubChem. "Isosaponarin." (Feb. 16, 2019). Accessed Feb. 17, 2019. Available from: <https://pubchem.ncbi.nih.gov/compound/Isosaponarin#section=Top>.
English translation of the Interntional Preliminary Report on Patentability Chapter I of the International Search Authority dated Jun. 5, 2018, for corresponding International Application PCT/JP2016/085968, filed Dec. 2, 2016.
Notice of Reasons for Rejection issued in corresponding JP Patent Application No. 2017-554213 dated Sep. 4, 2018.
Notice of Final Rejection and its English translation issued in related Korean patent application No. 10-2017-7035903 dated Sep. 28, 2019.
Office Action issued in the counterpart Chinese Application No. 201680034927.4 dated Mar. 9, 2020.
Office Action in the counterpart Brazilian Application No. 1120170271478 dated Jun. 17, 2020.
Office Action in the counterpart Chinese Application No. 201680034927.4 dated Jul. 31, 2020 and its English translation.
Office Action in the counterpart European Application No. 16870840.2 dated Nov. 27, 2020.
Notice of Reasons for Refusal issued for counterpart Japanese Patent Application No. 2019-220346, dated Feb. 9, 2021.
Decision of Rejection issued for counterpart Chinese Application No. 201680034927.4, dated Apr. 15, 2021.

```
                              SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Synthetic DNA

<400> SEQUENCE: 1
tctgtcgaac acagtggtac ctgag                                          25

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
gccactgtcc tgatttccat ga                                             22

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
catccctgcc tctactggcg ctgcc                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
ccaggatgcc cttgaggggg ccctc                                          25
```

HAIR RESTORATION/GROWTH STIMULATING AGENT

CROSS-REFERENCE TO RELATED APPLICATION

This application is a continuation of U.S. patent application Ser. No. 15/737,097, filed Dec. 15, 2017, which is a Section 371 National Stage Application of International Application No. PCT/JP2016/085968, filed Dec. 2, 2016, and published as WO2017/094905 A1, claims the benefit of Japanese Patent Application No. 2015-235965 filed on Dec. 2, 2015 with the Japan Patent Office, the entire disclosures of which are incorporated herein by reference.

TECHNICAL FIELD

The present disclosure relates to a hair restoration/growth stimulating agent.

BACKGROUND ART

Hair repeats growing and falling out in accordance with a periodic hair cycle including a growth phase (anagen), an involuting phase (catagen), and a resting phase (telogen). Various cells are active during the hair cycle, but follicle dermal papilla cells play the most important role in controlling the hair cycle. Follicle dermal papilla cells are cells located at fundamental parts of hair roots. Follicle dermal papilla cells play an important role in hair differentiation, such as acting on hair matrix cells existing around follicle dermal papilla cells to promote proliferation of hair matrix cells.

Hair loss occurs due to aging, stress caused by living environment factors, collapse of hormonal balance, side effects of drugs, and the like. When the metabolism of follicle dermal papilla cells decreases due to such various causes, activation and differentiation of hair matrix cells are inhibited. Hair loss occurs by shortening of duration of the hair cycle.

In recent years, men and women suffering from thin hair and hair loss are on an increasing trend due to various factors such as an increase in stress and a change in dietary habits. Expectation for a hair restoration/growth stimulating agent is increasing. Various hair restoration/growth stimulating agents have been developed in response to such social demands.

For example, minoxidil (chemical name: 6-(1-piperidinyl)-2,4-pyrimidinediamine-3-oxide) and adenosine related compounds, and the like are known as active ingredients of hair restoration/growth stimulating agents.

It is known that minoxidil promotes blood circulation by expanding peripheral blood vessels and promotes hair growth by stimulating follicle dermal papilla cells. Furthermore, it has been reported that adenosine and derivatives thereof act on adenosine receptors of follicle dermal papilla cells to promote production of fibroblast growth factor, and are effective to activate hair matrix cells (see Patent Document 1).

PRIOR ART DOCUMENTS

Patent Documents

Patent Document 1: Japanese Patent Application Publication No. 2000-297015

SUMMARY OF THE INVENTION

Problems to be Solved by the Invention

The known hair restoration/growth stimulating agent as described above has not yet satisfied the demands of consumers. Due to such circumstances, a hair restoration/growth stimulating agent that is more effective in stimulating hair restoration/growth has been desired in the market.

Means for Solving the Problems

In order to solve the problem as above, the present inventors conducted extensive research and found that flavonoid and phenylpropanoid, which have been hitherto unknown at all in relation to hair growth action, have hair restoration effects.

That is, one aspect of the present disclosure provides a hair restoration/growth stimulating agent containing at least one type of flavonoid represented by the following formula (I) as an active ingredient.

[Formula 1]

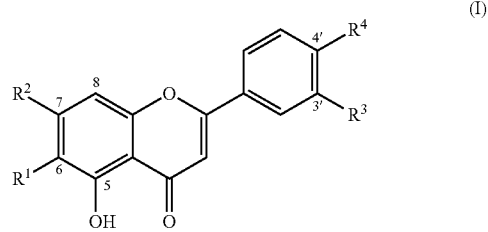

In the above formula (I), $R^1$ is a glycosyl, glycosyl-glycosyl-O-sinapoyl or H, $R^2$ is O-sinapoyl or OH, $R^3$ is H or OH, $R^4$ is O-glycosyl, OH or O-glycosyl-synapoyl.

One aspect of the present disclosure provides a hair restoration/growth stimulating agent containing at least one type of phenylpropanoid represented by the following formula (II) as an active ingredient.

[Formula 2]

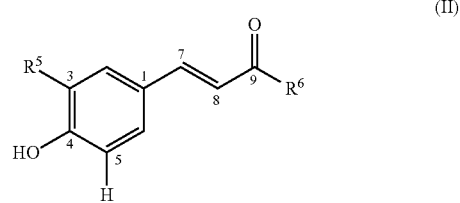

In the above formula (II), $R^5$ is H or OH, $R^6$ is OH or $OCH_3$.

According to the results of research by the present inventors, at least one type of flavonoid represented by the above formula (I) and at least one type of phenylpropanoid represented by the above formula (II) have a function to activate follicle dermal papilla cells. Existence of the function as such is apparent from Examples to be described later. Therefore, extremely excellent hair restoration/growth effect can be expected from use of a hair restoration/growth stimulating agent containing the flavonoid and the phenylpropanoid as active ingredients.

MODE FOR CARRYING OUT THE INVENTION

Figure 1:
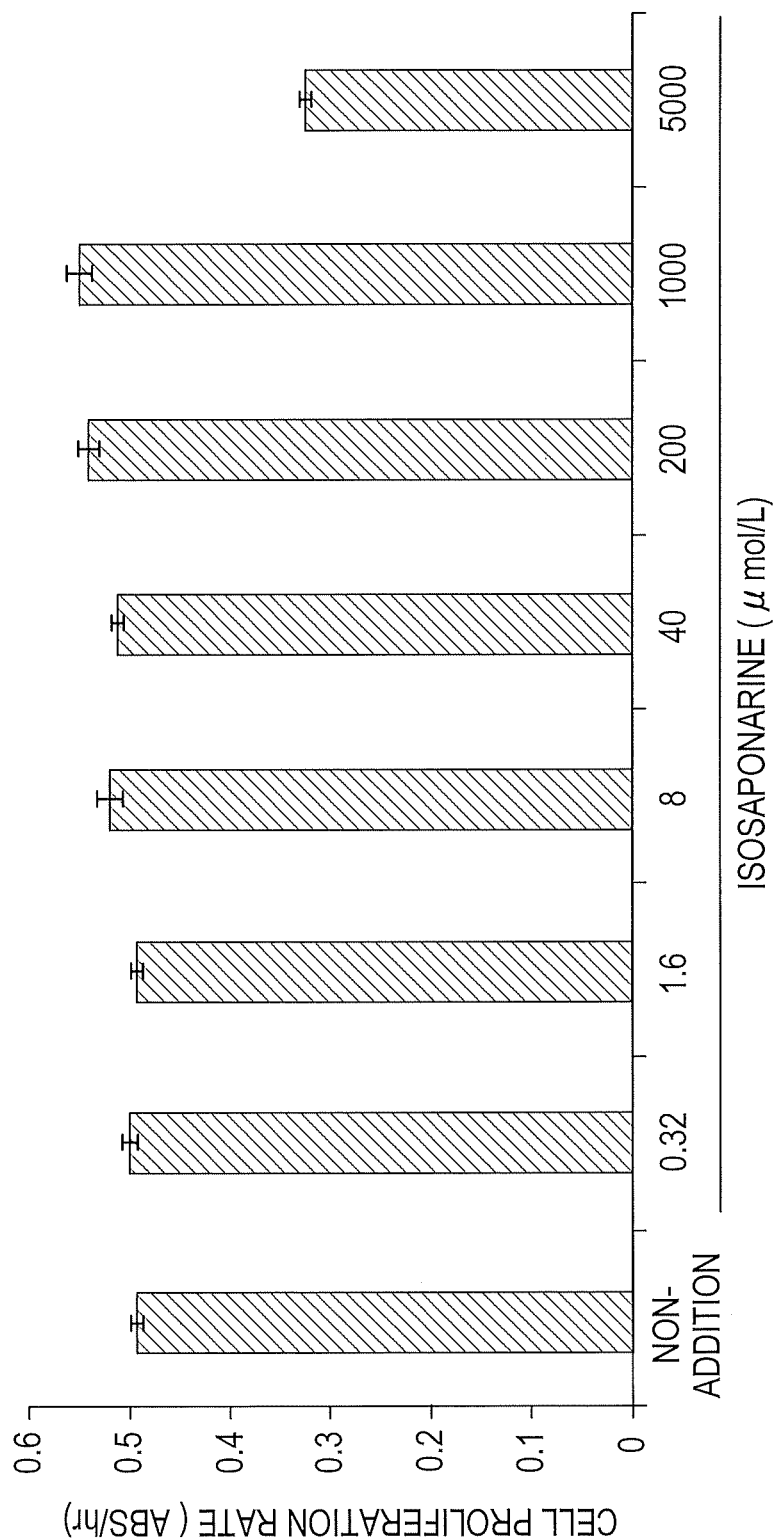
FIG. 1 is a graph showing results of a cytotoxicity test of isosaponarin using human hair follicle dermal papilla cells.

The hair restoration/growth stimulating agent of the present disclosure contains at least one type of flavonoid represented by the above formula (I) as an active ingredient. In addition, the hair restoration/growth stimulating agent of the present disclosure contains at least one type of phenylpropanoid represented by the above formula (II) as an active ingredient. Here, "contain" means that the hair restoration/growth stimulating agent of the present disclosure may contain one or more types of flavonoids, and may also contain ingredients other than one or more types of flavonoids. In addition, the "hair restoration/growth stimulating agent" of the present disclosure is a substance that exerts hair restoration effect, hair growth effect, and hair restoration and growth effect by a mechanism described later. Hair restoration effect means an effect of developing hair, preventing hair loss, and reducing hair loss. Hair growth effect means an effect of generating hair. Therefore, the hair restoration/growth stimulating agent of the present disclosure can be used as any of a hair restoration agent, a hair growth agent, and a hair restoration and growth agent.

The flavonoid represented by the above formula (I), for example, includes: isosaponarin represented by the above formula (I) where $R^1$ is glycosyl, $R^2$ is OH, $R^3$ is H, and $R^4$ is O-glycosyl [also known as isovitexin 4'-O-β-D-glucopyranoside]; 7-O-trans-sinapoylisovitexin4'-O-β-D-glucopyranoside represented by the above formula (I) where $R^1$ is glycosyl, $R^2$ is O-sinapoyl, $R^3$ is H, and $R^4$ is O-glycosyl; 7-O-trans-sinapoylisovitexin represented by the above formula (I) where $R^1$ is glycosyl, $R^2$ is O-sinapoyl, $R^3$ is H, and $R^4$ is OH; 7-O-trans-sinapoylisovitexin4'-O-(6-O-trans-sinapoyl-β-D-glucopyranoside) represented by the above formula (I) where $R^1$ is glycosyl, $R^2$ is O-sinapoyl, $R^3$ is H, and $R^4$ is O-glycosyl-sinapoyl; 6"-O-(2-O-trans-sinapoyl-β-D-glucopyranosyl)-7-O-trans-sinapoylisovitexin represented by the above formula (I) where $R^1$ is a glycosyl-glycosyl-O-sinapoyl, $R^2$ is O-sinapoyl, $R^3$ is H, and $R^4$ is OH; 6"-O-(2-O-trans-sinapoyl-β-D-glucopyranosyl)-7-O-trans-sinapoylisovitexin 4'-O-β-D-glucopyranoside represented by the above formula (I) where $R^1$ is a glycosyl-glycosyl-O-sinapoyl, $R^2$ is O-sinapoyl, $R^3$ is H, and $R^4$ is O-glycosyl; isovitexin represented by the above formula (I) where $R^1$ is glycosyl, $R^2$ is OH, $R^3$ is H, and $R^4$ is OH; isoorientin represented by the above formula (I) where $R^1$ is glycosyl, $R^2$ is OH, $R^3$ is OH, and $R^4$ is OH; isoorientin4'-O-β-D-glucopyranoside represented by the above formula (I) where $R^1$ is glycosyl, $R^2$ is OH, $R^3$ is OH, and $R^4$ is O-glycosyl; apigenin represented by the above formula (I) where $R^1$ is H, $R^2$ is OH, $R^3$ is H, and $R^4$ is OH [also known as 2-(4-hydroxyphenyl)-5-hydroxy-7-hydroxy-4H-1-benzopyran-4-one; luteolin represented by the above formula (I) where $R^1$ is H, $R^2$ is OH, $R^3$ is OH, and $R^4$ is OH [also known as 2-(3-hydroxy-4-hydroxyphenyl)-5-hydroxy-7-hydroxy-4H-1-benzopyran-4-one], and the like. Further, the flavonoid represented by the formula (I) is preferably isosaponarin. The name based on IUPAC of isosaponarin is 4'-(β-D-glucopyranosyloxy)-5,7-dihydroxy-6-β-D-glucopyranosyl-flavone. These flavonoids can be used alone, or in combination of multiple kinds.

The phenylpropanoid represented by the above-mentioned formula (II), for example, includes: coumaric acid represented by the above formula (II) where $R^5$ is H, $R^6$ is OH; caffeic acid methyl ester represented by the above formula (II) where $R^5$ is OH, $R^6$ is $OCH_3$, and the like. These phenylpropanoids can be used alone, or in combination of multiple kinds. The flavonoid and the phenylpropanoid may also be used in combination with each other.

The flavonoid represented by the above formula (I) and the phenylpropanoid represented by the above formula (II) can be obtained by chemical synthesis, but may be extracted/purified from plants. Such plants, for example, include Brassicaceae plants, Caryophyllaceae plants (cowherb, academic name: Vaccaria segetalis), Umbelliferae plants, Gramineae plants, Capparidaceae plants, Caricaceae plants, Resedaceae plants, Tropaeolaceae plants, etc. Therefore, the flavonoid represented by the above formula (I) and the phenylpropanoid represented by the above formula (II) may be ingredients extracted from at least one of the above plants. For example, the flavonoid represented by the above formula (I) and the phenylpropanoid represented by the above formula (II) are ingredients extracted from at least one of wasabi (Wasabia japonica) [also known as hon-wasabi] and horseradish (Armoracia rusticana) [also known as yama-wasabi].

A method of extraction/purification from the plants, for example, includes extracting the flavonoid represented by the above formula (I) and the phenylpropanoid represented by the above formula (II), for example, from wasabi or horseradish. In particular, a method for extracting isosaponarin from hon-wasabi is disclosed in WO 2011/058661. Isosaponarin is contained more in extracts from hon-wasabi than any flavonoid represented by the formula (I) other than isosaponarin. Therefore, isosaponarin may be an ingredient extracted from hon-wasabi.

It has been found that the flavonoid represented by the above formula (I) activates follicle dermal papilla cells as shown in Example 1 below.

In addition, it has been found that the flavonoid represented by the above formula (I) increases an amount of vascular endothelial growth factor (VEGF) in follicle dermal papilla cells as shown in Example 2 below.

As shown in Example 7 below, the phenylpropanoid represented by the above formula (II) has been found to be effective for activating follicle dermal papilla cells, increasing the amount of VEGF production, and increasing the expression level of FGF-7 gene.

VEGF is known to act on vascular endothelial cells to promote proliferation and migration of cells, encourage angiogenesis, and enhance vascular permeability. VEGF is produced in every cell, but also from follicle dermal papilla cells. It is thought that VEGF produced from follicle dermal papilla cells promote angiogenesis, thereby activating hair matrix cells around follicle dermal papilla cells to stimulete hair growth. Therefore, it is thought that having VEGF production promoting action contributes to hair matrix cell-activating action, hair growth stimulating action and the like.

FGF-7 is a fibroblast growth factor secreted from follicle dermal papilla cells. It is thought that FGF-7 acts on hair matrix cells to promote their proliferation, thereby stimulating hair growth, and thus is effective during growth phase in hair cycle.

The flavonoid represented by the above formula (I) is thought to have very good hair restoration/growth action, since they have cell-activating action and VEGF production promoting action on follicle dermal papilla cells, as described above. Therefore, since the hair restoration/growth stimulating agent of the present disclosure contains the flavonoid represented by the above formula (I), it exhibits excellent hair restoration effect, hair growth effect, and hair restoration and growth effect. Also, the phenylpropanoid represented by the above formula (II) is thought to have very good hair restoration/growth action, since it has follicle dermal papilla cell-activating action, VEGF production promoting action and FGF-7 gene promoting action, as described above. Therefore, since the hair restoration and growth stimulating agent of the present disclosure contains the phenylpropanoid represented by the above formula (II), it exhibits excellent hair restoration effect, hair growth effect, hair restoration/growth effect. In addition, the hair restoration/growth stimulating agent of the present disclosure can be also used as a follicle dermal papilla cell activation promoting agent and a VEGF production promoting agent for follicle dermal papilla cells.

The flavonoid represented by the above formula (I) can be incorporated in cosmetics, quasi-drugs and pharmaceuticals, or foods. In addition, the phenylpropanoid represented by the above formula (II) can be incorporated in cosmetics, quasi-drugs and pharmaceuticals, or foods. Therefore, the hair restoration/growth stimulating agent of the present disclosure can be used as cosmetics, quasi-drugs, pharmaceuticals, or foods.

When the hair restoration/growth stimulating agent of the present disclosure is implemented in the form of cosmetics, quasi-drugs, pharmaceuticals, it may be used as an external preparation for skin. However, the hair restoration/growth stimulating agent is not limited to external preparations for skin because it can be taken orally.

In the case of implementing the hair restoration/growth stimulating agent of the present disclosure in the form of cosmetics, the content of the flavonoid in the cosmetics is preferably 0.001 µmol/L to 5,000 µmol/L, and more preferably 0.1 µmol/L to 1,000 µmol/L. In the case of implementing the hair restoration/growth stimulating agent of the present disclosure in the form of quasi-drugs, the content of the flavonoid in the quasi-drugs is preferably 0.001 µmol/L to 5,000 µmol/L, and more preferably 0.1 µmol/L to 1,000 µmol/L. In the case of implementing the hair restoration/growth stimulating agent of the present disclosure in the form of pharmaceuticals, the content of the flavonoid in the pharmaceuticals is preferably from 0.1 mg to 5.0 g, and more preferably from 0.2 mg to 1.0 g. Daily dosage of the pharmaceuticals per adult is preferably 1 mg to 10 g, and more preferably 20 mg to 1.0g.

When the hair restoration/growth stimulating agent of the present disclosure is implemented in the form of foods, it may be used as functional foods, for example, foods for specified health use or foods with functional claims. In the case where the hair restoration/growth stimulating agent of the present disclosure is implemented in the form of foods, the content of the flavonoid in the foods is preferably from 0.1 mg to 5.0 g, and more preferably from 0.2 mg to 1.0 g.

In addition to the flavonoid represented by the above formula (I) as an active ingredient, various optional ingredients generally used for cosmetics, quasi-drugs, pharmaceuticals, or foods may be appropriately blended in the hair restoration/growth stimulating agent of the present disclosure as necessary, within a range not to impair the effect of the present disclosure. In addition to the phenylpropanoid represented by the formula (II) as an active ingredient, various optional ingredients generally used for cosmetics, quasi-drugs, pharmaceuticals, or foods may be appropriately blended in the hair restoration/growth stimulating agent of the present disclosure as necessary, within a range not to impair the effect of the present disclosure. For example, the following example ingredients and additives may be freely selected and used in combination. Further, for the purpose of enhancing the hair restoration/growth effect, predetermined medicinal ingredients such as antioxidants, physiologically active substances, and ingredients known to be effective for hair restoration/growth may be blended. As a result, synergistic effect with the ingredients of the present disclosure may be exerted, leading to an excellent use effect more than expected.

Example fats and oils include soybean oil, evening primrose oil, rice germ oil, rice bran oil, wheat germ oil, avocado oil, grapeseed oil, camellia oil, jojoba oil, shiso oil, olive oil, sesame oil, cacao oil, chamomile oil, carrot oil, cucumber oil, tallow fatty acid, coconut oil, safflower oil, corn oil, rapeseed oil, castor oil, cottonseed oil, peanut oil, mink oil, egg yolk oil, palm oil, palm kernel oil, coconut oil, tallow, lard, shea butter, squalene, squalane, pristane or hydrogen additives of these oils and fats (hydrogenated oil etc.)

Example waxes include beeswax, bleached beeswax, carnauba wax, whale wax, lanolins, candelilla wax, montan wax, shellac wax, rice wax and the like.

Example mineral oils include liquid paraffin, vaseline, paraffin, ozokerite, ceresin, microcrystalline wax and the like.

Example fatty acids include natural fatty acids such as lauric acid, myristic acid, palmitic acid, stearic acid, behenic acid, oleic acid, linoleic acid, linolenic acid, docosahexaenoic acid, eicosapentaenoic acid, lanolin fatty acid and the like, fatty acids such as isopentanoic acid and the like.

Example alcohols include ethanol, isopropanol, ethylene glycol, lauryl alcohol, cetanol, stearyl alcohol, oleyl alcohol, lanolin alcohol, cholesterol, phenoxyethanol, 2-hexyldecanol, isostearyl alcohol, 2-octyldodecanol, and the like. Examples of polyhydric alcohols include ethylene glycol, diethylene glycol, triethylene glycol, ethylene glycol monoethyl ether, ethylene glycol monobutyl ether, polyethylene glycol, propylene oxide, propylene glycol, polypropylene glycol, 1,3-butylene glycol, pentyl glycol, glycerin, pentaerythritol, threitol, arabitol, xylitol, galactitol, sorbitol, mannitol, lactitol, maltitol, and the like.

Example esters include isopropyl myristate, isopropyl palmitate, butyl stearate, hexyl laurate, myristyl myristate, oleyl oleate, decyl oleate, octyl dodecyl myristate, hexyl decyl dimethyl octanoate, cetyl lactate, myristyl lactate, diethyl phthalate, dibutyl phthalate, lanolin acetate, ethylene glycol monostearate, propylene glycol monostearate, glyceryl monostearate, propylene glycol dioleate and the like.

Example metal soaps include aluminum stearate, magnesium stearate, zinc stearate, calcium stearate, zinc palmitate, magnesium myristate, zinc laurate and the like.

Example gums, saccharides or water-soluble polymer compounds include gum arabic, xanthan gum, guar gum, karaya gum, agar, casein, lactose, fructose, sucrose or an ester thereof, trehalose or derivatives thereof, dextrin, gelatin, pectin, starch, carrageenan, chitin or chitosans, alginic acid, hyaluronic acid and chondroitin sulfuric acid or salts thereof, heparin, ethylcellulose, methylcellulose, carboxymethylcellulose, carboxyethylcellulose, crystalline cellulose, β-glucan, polyvinyl alcohol, polyvinyl methyl ether, polyacrylate, polyalkylene oxide or crosslinked polymers thereof, carboxyvinyl polymers, and the like.

Example surfactants include anionic surfactants such as alkylcarboxylate, alkylsulfonate, alkylsulfate ester salts, and alkylphosphate ester salts; cationic surfactants such as alkylamine salts, and alkyl quaternary ammonium salts, amphoteric surfactants such as carboxylic acid type amphoteric surfactants, sulfate ester type amphoteric surfactants, and sulfonic acid type amphoteric surfactants, phosphate ester type amphoteric surfactants, and nonionic surfactants; and other surfactants such as natural surfactants, derivatives of protein hydrolysates, polymeric surfactants, surfactants including titanium and silicon, fluorocarbon surfactants, and the like.

Example vitamins include vitamin A group such as retinol, retinal, dehydroretinal, carotene, and lycopene; vitamin B group such as thiamine hydrochloride, thiamine sulfate, riboflavin, pyridoxine, cyanocopalamin, and folic acids; vitamin C; biotin; pantothenic acid; vitamin C derivatives such as ascorbyl magnesium phosphate, sodium ascorbyl phosphate, ascorbyl tetrahexyl decanoate; vitamin D group, vitamin E group and derivatives thereof; vitamin K group; and others such as essential fatty acids, carnitine, ferulic acid, γ-oryzanol, vitamin P group, vitamin U group, and the like.

Example amino acids include valine, leucine, isoleucine, threonine, methionine, phenylalanine, tryptophan, lysine, glycine, alanine, asparagine, glutamine, serine, cysteine, cystine, tyrosine, proline, hydroxyproline, aspartic acid, glutamic acid, arginine, ornithine, histidine and the like, or sulfate, phosphate, and nitrate thereof, citric acid, and amino acid derivatives such as pyrrolidone carboxylic acid and the like.

Example ultraviolet absorbing/blocking agents include β-isopropyl furanone derivatives, urocanic acid, ethyl urocaninate, octyl para-dimethylbenzoate, benzophenone derivatives such as 2-hydroxy-4-methoxybenzophenone, and 2-hydroxy-4-methoxybenzophenone-5-sulfonic acid, para-aminobenzoic acid, para-aminobenzoic acid derivatives such as ethyl para-aminobenzoate, methoxycinnamic acid derivatives such as ethyl para-methoxycinnamate and isopropyl para-methoxycinnamate, salicylic acid derivatives, anthranilic acid derivatives, urocanic acid derivatives, coumarin derivatives , amino acid compounds, benzotriazole derivatives, tetrazole derivatives, imidazoline derivatives, pyrimidine derivatives, dioxane derivatives, camphor derivatives, furan derivatives, pyrone derivatives, nucleic acid derivatives, allantoin derivatives, nicotinic acid derivatives, vitamin B6 derivatives, umbelliferone, esculin, benzyl cinnamate, cinoxate, oxybenzone, dioxybenzone, octabenzone, slissobenzone, benzoresorcinol, arbutin, guaiazulene, shikonin, baicalin, baicalein, berberine, neoheriopan, escalol, zinc oxide, titanium oxide, talc, kaolin and the like.

Example metabolic promoting/cell activating substance include hydroquinone, lactic acid bacteria extract, placenta extract, ganoderma lucidum extract, vitamin A, vitamin E, allantoin, spleen extract, thymus extract, yeast extract, fermented milk extract, plant extract (aloe, scutellaria root, field horsetail, gentian, burdock, lithospermum root, carrot, hamamelis, hops, coix seed, dead nettle, swertia japonica, Japanese angelica root, calendula officinalis, hydrangea, hypericum erectum, cucumber, thymus vulgaris, rosemary, parsley) and the like.

For example, as active oxygen eliminators, astringents such as succinic acid, tannic acid, allantoin, zinc chloride, and zinc sulfate are also used. The examples are superoxide dismutase (SOD), catalase, glutathione peroxidase, and the like.

Example antioxidants include vitamin C or salts thereof, stearic acid ester, vitamin E or derivatives thereof, nordihydroguar cetenoic acid, butylhydroxytoluene (BHT), butylhydroxyanisole (BHA), hydroxytyrosol, para-hydroxyanisole, propyl gallate, sesamol, sesamolin, gossypol, propolis, and the like.

Example lipid peroxide production inhibitors include β-carotene, plant extracts (sesame, hydrangea, hypericum erectum, hamamelis, clove, lemon balm, plectranthus, white birch, scarlet sage, rosemary, nandina fruit, rose fruit, gingko, green tea) and the like.

Example anti-inflammatory agents include ichthammol, indomethacin, kaolin, salicylic acid, sodium salicylate, methyl salicylate, acetylsalicylic acid, diphenhydramine hydrochloride, d-camphor, dl-camphor, hydrocortisone, guaiazulene, chamazulene, chlorpheniramine maleate, glycyrrhizic acid or salts thereof, glycyrrhetinic acid or salts thereof, licorice extract, lithospermum root extract, rose fruit extract, saxifrage extract, shiso extract, coix seed extract, propolis, and the like.

Example antibacterial agents/disinfectants include hinokitiol, acrinol, sulfur, calcium gluconate, chlorhexidine gluconate, sulfamine, mercurochrome, lactoferrin or hydrolyzate, chlorides alkyldiaminoethylglycine solution, triclosan, sodium hypochlorite, chloramine T, calcium hypochlorite, iodine compounds, iodoform, sorbic acid or salts, propionic acid or salts, salicylic acid, dehydroacetic acid, benzoic acid, sodium benzoate, p-hydroxybenzoic acid esters, undecylenic acid, thiamine laurylsulfate, thiamine lauryl nitrate, phenol, cresol, p-chlorophenol, p-chloro-m-xylenol, p-chloro-m-cresol, thymol, phenethyl alcohol, O-phenylphenol, Irgas an CH3565, halocarban, hexachlorophene, chlorhexidine, ethanol, methanol, isopropyl alcohol, benzyl alcohol, ethylene glycol, propylene glycol, phenoxyethanol, 1,2-pentanediol, zinc pyridione, chlorobutanol, isopropyl methylphenol, nonionic surfactants such as polyoxyethylene lauryl ether, amphoteric surfactants, anionic surfactants such as sodium lauryl sulfate, cationic surfactants such as benzalkonium chloride, formaldehyde, hexamine, photosensitizer 101, photosensitizer 201, photosensitizer 401, N-long chain acyl basic amino acid derivatives and acid addition salts thereof, zinc oxide, hinokitiol, sophora root, propolis, oil-soluble licorice extract and the like Example humectants include glycerine, propylene glycol, 1,3-butylene glycol, polyethylene glycol, caprylic/capric triglyceride, glycolic acid(-hydroxy acid), hyaluronic acid or salts thereof, chondroitin sulfate or salts thereof, water-soluble chitin or derivatives thereof, or chitosan derivatives, pyrrolidone carboxylic acid or salts thereof, sodium lactate, urea, sorbitol, amino acids or derivatives thereof, fats (including hydrogenated oils) such as olive oil, chamomile oil, orcastor oil, waxes such as beeswax, lanolin, or shellac wax, mineral oils such as liquid paraffin, petrolatum,or paraffin, plant extracts such as natto metabolite, natto extract, silk fiber extract, chamomile, or aloe, and the like.

Example keratolytic agents include elastase activity inhibitors such as diisopropyl fluorophosphate, plant extracts (scutellaria root, hypericum erectum, sophora flavescens, mulberry leaves, cassia, geranium herb, comfrey, scarlet sage, sambucus nigra, lime, moutan bark), and seaweed extracts; peripheral vascular blood flow enhancers such as vitamin E or derivatives thereof, swertia japonica extract, garlic extract, ginseng extract, aloe extract, gentiana extract, Japanese angelica root extract, cepharanthine, carpronium chloride, and minoxidil; stimulants such as capsicum tincture, vanillamide nonyl acid, cantharis tincture, ginger tincture, peppermint oil, 1-menthol, camphor, and benzyl nicotinate, anti-seborrhoeic agents such as pyridoxine or derivatives thereof, sulfur, and vitamin B6; resorcin, salicylic acid, lactic acid, urea, and the like.

Example perfumes include natural animal perfumes such as musk; vegetable perfumes such as menthol, spearmint, peppermint, anise essential oil, orange essential oil, cardamom essential oil, guaiacwood essential oil, cumin essential oils, cassia essential oils, cinnamon essential oil, geranium essential oil, coriander essential oil, shiso essential oil, cedarwood essential oil, citronella essential oil, jasmine essential oil, ginger grass essential oil, cedar essential oil, spearmint essential oil, peppermint essential oil, neroli essential oil, wintergreen essential oil, rose essential oil, cypress essential oil, thujopsis essential oil, sandalwood essential oil, bay essential oil, bergamot essential oil, eucalyptus essential oil, lime essential oil, lavender essential oil, lemon essential oil, rosemary essential oil, and Japanese mint essential oil; other synthetic perfumes and the like.

Example hormones include estradiol and esters thereof, estrone, ethinyl estradiol, cortisone and esters thereof, hydrocortisone and esters thereof, buredonizon, prednisolone, and the like.

Example ingredients generally known to be effective in hair restoration/growth include pentadecanoic acid glyceride, coleus extract, gentiana extract, pine cone extract, royal jelly extract, sasa veitchii leaf extract, t-flavanone, 6-benzylaminopurine, swertia japonica extract, carpronium chloride, minoxidil, finasteride, adenosine, nicotinic acid amide, mulberry root extract, rehmannia glutinosa root extract, 5-aminolevulinic acid and the like.

Other examples include metal ion sequestering agents, pH adjusting agents, chelating agents, antiseptic/antifungal agents, fresheners, stabilizers, emulsifiers, animal/plant proteins and degradation products thereof, animal/plant polysaccharides and decomposition products thereof, animal and vegetable/plant glycoprotein and degradation products thereof, blood flow accelerators, anti-inflammatory agents, antiphlogistic agents, preservatives, antiallergic agents, wound healing agents, foam boosters, thickeners, enzymes, dyes, purified water, oral agents, antiphlogistic/deodorizing agent, bittering agent, and the like.

Further, the usage form of the hair restoration/growth stimulating agent of the present disclosure is not limited. Specifically, example cosmetics, quasi-drugs, and pharmaceuticals include internal/external preparation, toner, milky lotion, cream, ointment, lotions, oils, packs, skin cleaning agents, shampoos, rinses, hair treatments, hair cream, pomade, hair spray, hair dressing, perming agents, hair restoration agent, hair dye, and the like. Example foods include health functional foods and special purpose foods such as foods for health foods, foods with functional claims, specified health use, liquid foods such as soft drinks, tea drinks, health drinks, and alcoholic beverages; confectionery, cooked rice, bread, noodles, prepared foods, seasonings, and the like.

In case that the hair restoration/growth stimulating agent of the present disclosure is implemented in the form of cosmetics, quasi-drugs, and pharmaceuticals, its dosage form is not limited and may vary. Example dosage forms include ampoule, capsule, powder, granule, pill, tablet, solid, liquid, gel, bubble, milky lotion, cream, ointment, sheet, and mousse.

The present disclosure will be explained in more detail, referring to

Examples below. However, the present disclosure is not limited by the following Examples.

EXAMPLE 1

Evaluation of Follicle Dermal Papilla Cell-Activating Action (1-1) Culture Method of Human Hair Follicle Dermal Papilla Cell Human hair follicle dermal papilla cells (Cat. No. CA60205a, Lot No. 2548, derived from Caucasian 47-year-old female, distributed by Toyobo Co., Ltd.), which are widely used in efficacy evaluation of a hair restoration agent, were used as test cells. The human hair follicle dermal papilla cells were cultured in a carbon dioxide incubator (5% $CO_2$, 37° C.) using a follicle dermal papilla cell proliferation medium (Cat. No. TMTPGM-250, distributed by Toyobo Co., Ltd.) A flask used for the culture was coated with collagen I before use. For cell passage, cells were separated from the flask using a follicle dermal papilla cell dedicated subculture set (Cat. No. CA090K, distributed by Toyobo Co., Ltd.)

(1-2) Cytotoxicity Test of Human Hair Follicle Dermal Papilla Cell

This Example used isosaponarin as a test substance. The presence or absence of toxicity to human hair follicle dermal papilla cells was evaluated for the test substance.

The human hair follicle dermal papilla cells were seeded in a collagen I-coated 96-well plate at $5 \times 10^3$ cells/well (0.1 mL/well in this test). After one-day culturing (50% confluent) in the carbon dioxide incubator (5% $CO_2$, 37° C.), the cells were transferred to a test medium containing isosaponarin, and then cultured for three days. Cell proliferation was compared using Living Cell Count Reagent SF (Cat. No. 07553, distributed by Nacalai Tesque, Inc.) In consideration of possible influence on absorbance by precipitates adhering to the cells in absorbance measurement in living cell count, the culture supernatant was removed after the end of the three-day culturing, and the cells were washed with a phosphate-buffered saline (PBS). After washing with PBS, 100pL per well of a medium containing 10% of Living Cell Count Reagent SF was added. Absorbance (measurement wavelength 450 nm, reference wavelength 595 nm) of the culture supernatant was measured 30 minutes and 90 minutes after the addition. An amount of change (ABS/hr) in absorbance ABS per hour was calculated from values at 90 minutes and 30 minutes. The experiment was carried out three times.

As shown in FIG. 1, isosaponarin at 1000 μmol/L or less showed no toxicity to human hair follicle dermal papilla cells. Therefore, in an evaluation experiment of isosaponarin described below, isosaponarin test concentrations of 0.1 μmol/L, 10 μmol/L, and 1000 μmol/L were used. These test concentrations were prepared from a stock solution in which isosaponarin (molecular weight 594.52) was dissolved in a follicle dermal papilla cell proliferation medium at 100 mmol/L.

(1-3) Evaluation of Human Hair Follicle Dermal Papilla Cell-Activating Action

Human hair follicle dermal papilla cells were seeded in a 48-well plate at $1.2 \times 10^4$ cells/well (0.3 mL/well in this test). After one-day culturing in the carbon dioxide incubator, the cells were transferred to a follicle dermal papilla cell proliferation medium in which isosaponarin was dissolved at final concentrations of 0.1 μmol/L, 10 μmol/L, and 1000 μmol/L. Then, the cells were cultured for one day and three days, and proliferation of each cell was compared using Living Cell Count Reagent SF. After the one-day and three-day culturing were completed, the supernatant culture was removed, and the cells were washed with PBS. After washing with PBS, a medium containing 10% Living Cell Count Reagent SF at 300 μL/well was added. The culture supernatant at 100 μL/well was transferred to another 96-well plate 30 and 90 minutes after the addition. Absorbance was measured at a microplate reader (measuring wavelength 450 nm, reference wavelength 595 nm). An amount of change in absorbance ABS per hour (ABS/hr) was calculated from values at 90 minutes and 30 minutes to evaluate cell-activating action. The experiment was carried out five times. A non-addition control section was used as a comparison control section of isosaponarin.

As a positive control, the same test was carried out also for the case of adding adenosine (Cat. No. 016-10493, distributed by Wako Pure Chemical Industries, Ltd.) at final concentration of 100 μmol/L and minoxidil (Cat. No. M4145-25MG, distributed by Sigma-Aldrich Japan Co., Ltd.) at final concentration of 30 μmol/L. Adenosine was dissolved in dimethyl sulfoxide (DMSO) and added to a test medium at final concentration of 0.1% DMSO. As a solvent control, 0.1% DMSO experimental section was provided. Minoxidil was dissolved in ethanol and added to a test medium at final concentration of 0.1% ethanol. In general, 0.1% or less ethanol concentration does not affect the cell function of follicle dermal papilla cells. Thus, a non-addition control section was used for a comparison control section of minoxidil.

Figure 2:
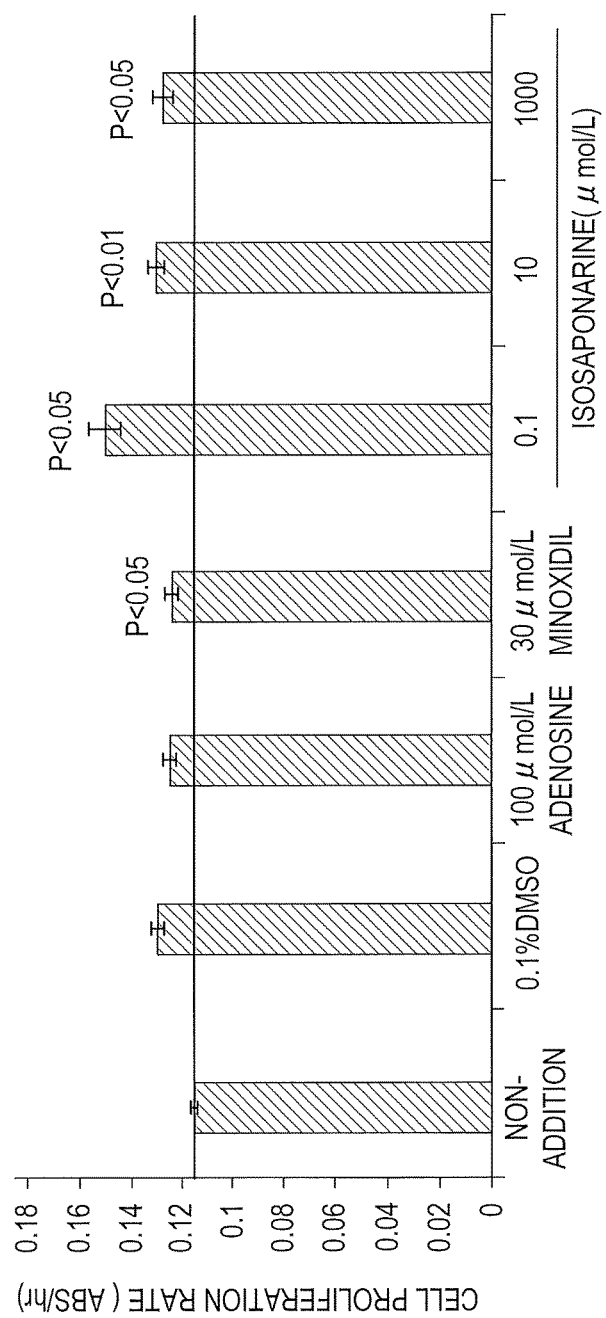
FIG. 2 is a graph showing results of studying cell-activating action one day after isosaponarin treatment using human hair follicle dermal papilla cells.
Figure 3:
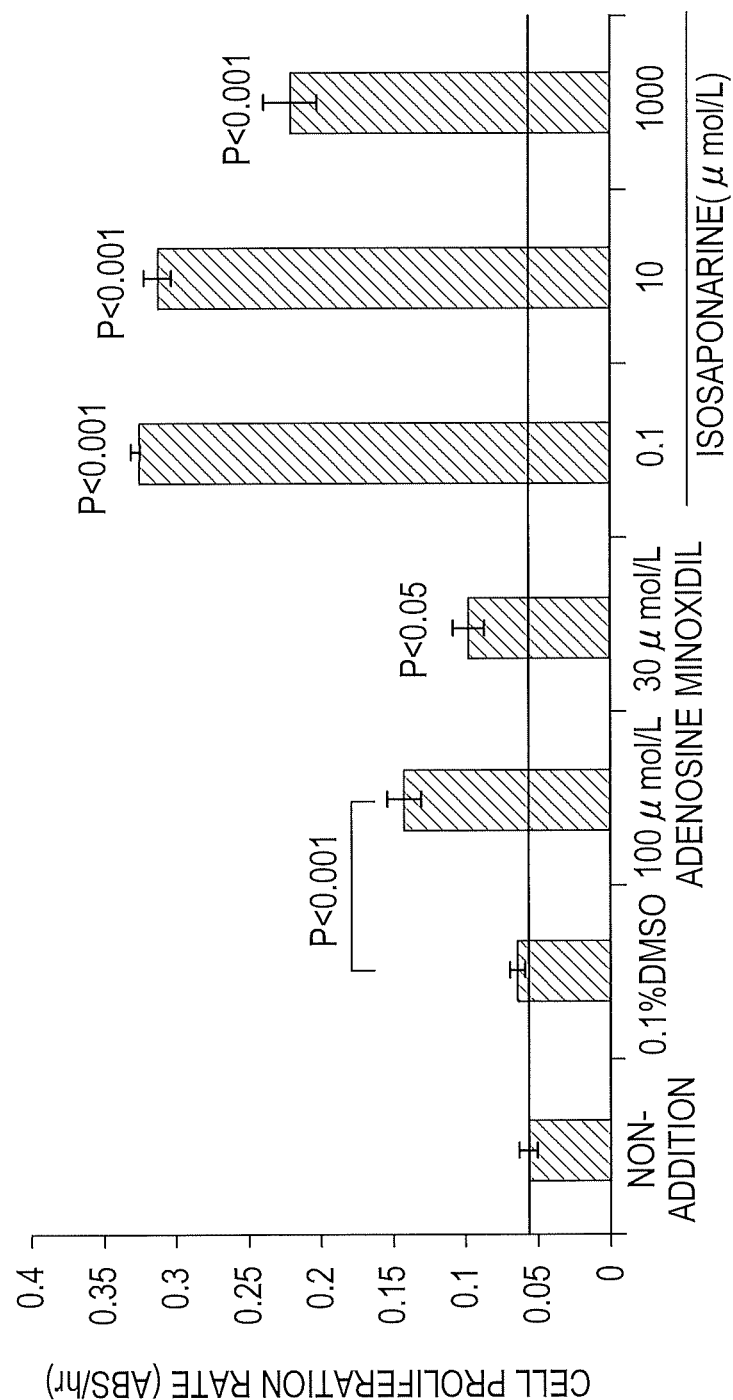
FIG. 3 is a graph showing results of studying cell-activating action three days after the isosaponarin treatment using human hair follicle dermal papilla cells.

Measurement results of the cells cultured for one day after addition of the test substance isosaponarin are shown in FIG. 2. Measurement results of the cells cultured for three days after addition of isosaponarin are shown in FIG. 3. Significance test was performed in the comparison experimental section. The test was carried out as Student T-test. It is determined that there is significance when $P<0.05$ (less than 5% if null hypothesis is true), as described in the figures.

As apparent from FIG. 2, in a one-day processing period, slightly more significant cell-activating action on human hair follicle dermal papilla cells was observed in a range of 0.1 μmol/L to 1000 μmol/L of a group treated with isosaponarin, than in the non-addition control section. Moreover, as is clear from FIG. 3, in a three-day processing period, more significant cell-activating action on human hair follicle dermal papilla cells was observed in a range of 0.1 μmol/L to 1000 μmol/L of the group treated with isosaponarin, than in the non-addition control section. The cell-activating action observed was about three times the action in the case of treating with minoxidil.

On the other hand, more significant cell-activating action on human hair follicle dermal papilla cells was observed in adenosine (positive control substance), in a three-day processing period, than in 0.1% DMSO experimental section. Further, slightly more significant cell-activating action on human hair follicle dermal papilla cells was observed in minoxidil (positive control substance), in a one-day processing period, than in the non-addition control section. In a three-day processing period, more significant cell-activating action on human hair follicle dermal papilla cells was observed in minoxidil than in the non-addition control section.

From this result, it was suggested that application of isosaponarin to a scalp or the like exhibits excellent follicle dermal papilla cell-activating action, and hair restoration effect and hair growth effect can be expected.

EXAMPLE 2

Evaluation of VEGF Production Promoting Action of Isosaponarin

An amount of VEGF produced by human hair follicle dermal papilla cells treated with isosaponarin was measured to evaluate VEGF production promoting action of isosaponarin on human hair follicle dermal papilla cells.

An amount of VEGF in a culture supernatant treated with isosaponarin for three days on human hair follicle dermal papilla cells was measured using ELISA kit for (product name: Human VEGF Quantikine ELISA, Cat. No. DVE00, distributed by R&D Systems, Inc.) The supernatant at the time of three-day culturing in the above section (1-3) was used as the culture supernatant treated with isosaponarin for three days. Specifically, in the above section (1-3), in order to measure absorbance, the culture supernatant was removed three days after addition of isosaponarin. In an evaluation test of VEGF production promoting action, the culture supernatant was collected three days after the addition of isosaponarin, and the supernatant was used as a sample. The experiment was carried out five times.

Hereinafter, a method of measuring VEGF will be described in detail. For the measurement of VEGF, the stock solution was used without diluting the supernatant.

Procedure 1-1. On the basis of a VEGF standard stock solution (2000 pg/mL), VEGF standard solutions of 1000, 500, 250, 125, 62.5, 31.2, and 15.6 pg/mL were prepared using a reaction buffer.

Procedure 1-2. Each of the VEGF standard solutions and 200 μL of sample (culture supernatant) were added to a VEGF immobilized microplate in which 50 μL of dilution was added to each well, and allowed to react at room temperature for 2 hours (primary reaction).

Procedure 1-3. The solutions in the wells were removed and the wells were washed 3 times with washing solution.

Procedure 1-4. 200 μL of horseradish peroxidase-conjugated VEGF antibody solution was added to each well and allowed to react for 2 hours at room temperature (secondary reaction).

Procedure 1-5. The solutions in the wells were removed and the wells were washed 3 times with the washing solution.

Procedure 1-6. 200 μL of substrate solution was added to each well and allowed to react for 20 minutes at room temperature.

Procedure 1-7. 50 μL of reaction stop solution was added to each well. After one minute mixing in a plate mixer, absorbance of each well was measured with a plate reader (measuring wavelength 450 nm).

Procedure 1-8. From a standard curve, VEGF concentration in the sample was calculated.

A non-addition control section was used as a comparison control section of isosaponarin.

As a positive control, the same experiment was performed to the case of adding minoxidil having final concentration of 30 μmol/L as well. A non-addition control section was used as a comparison control section of minoxidil.

Figure 4:
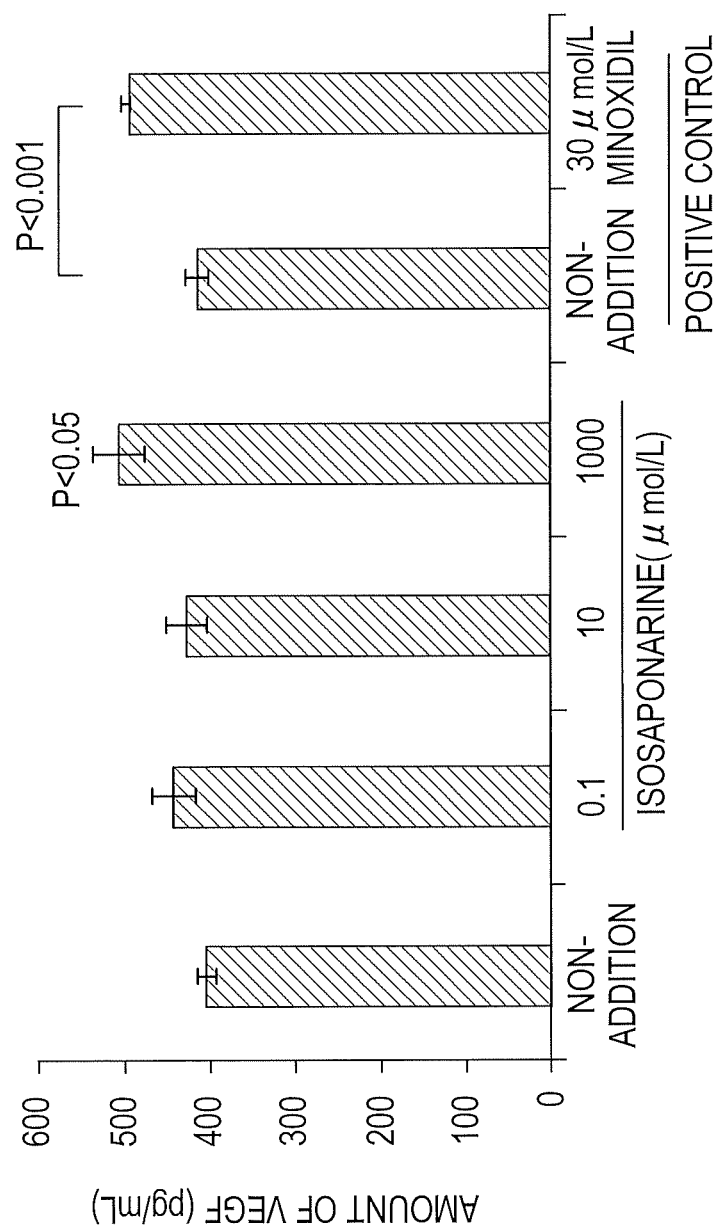
FIG. 4 is a graph showing results of studying VEGF production promoting action three days after the isosaponarin treatment using human hair follicle dermal papilla cells.

Results of measuring the amount of VEGF in the culture supernatant treated with the test substance for three days are as shown in FIG. 4. Similar to the above section (1-3), a significance test was performed, and results thereof were described in the figure.

As apparent from FIG. 4, with respect to human hair follicle dermal papilla cells, the amount of VEGF was significantly increased in a concentration group of isosaponarin at 1000 μmol/L, as compared to the non-addition control section. On the other hand, in the case of minoxidil (positive control substance), the amount of VEGF was significantly increased, as compared to the non-addition control section, with respect to human hair follicle dermal papilla cells.

From the results, it was suggested that application of isosaponarin to a scalp or the like increases the VEGF production amount, and excellent hair restoration effect and hair growth effect can be expected.

EXAMPLE 3

Production of Cosmetics

After washing with water, 100 kg of hon-wasabi was cut into pieces 1 cm wide, and pulverized with a cutter mixer. 200 kg of 50% butylene glycol was added to the pulverized hon-wasabi, and was stirred for an hour. Then, by squeezing, 180 kg of squeezed liquid was obtained. Furthermore, the squeezed liquid was sterilized by heating for 30 minutes at 90° C. to obtain an extract. The hon-wasabi extract obtained as such was used to produce hair cosmetics having a formulation shown below. A total amount is 100 g in the formulation below. 1.5 mg of isosaponarin is contained in 100 g of the hair cosmetics.
  Water 86.48 g
  Butylene glycol 5.0 g
  Glycerin 2.0 g
  Hon-wasabi extract 5.0 g
  Trehalose 1.0 g
  Phenoxyethanol 0.5 g
  Sodium citrate 0.01 g
  Citric acid 0.01 g

MODIFICATION OF EXAMPLE 3

Example 3 above shows an example of the cosmetics containing 1.5 mg of isosaponarin in 100 g of hair cosmetics, but this is not limited thereto. For example, 5 μg (0.1 μmol/L) to 59.0 mg (1,000 μmol/L) of isosaponarin may be contained in 100 mL of the cosmetics.

Further, Example 3 shows an example in which the hair cosmetics contain isosaponarin. The hair cosmetics may contain phenylpropanoid. Specifically, 100 mL of the hair cosmetics may contain 1.0 mg of phenylpropanoid. A content of phenylpropanoid is not limited thereto. For example, 100 mL of the cosmetics may contain 0.001 to 100 mg of phenylpropanoid.

EXAMPLE 4

Production of Food (1)

After washing with water, 100 kg of hon-wasabi was cut into 1 cm wide, and pulverized with a cutter mixer. 200 kg of 50% ethanol was added to the pulverized hon-wasabi, stirred for an hour, and then squeezed to obtain 180 kg of solution. After concentrating to remove alcohol content, the solution was sterilized by heating for 30 minutes at 90° C. After 10 kg of cellulose was added for kneading, the solution was dried and pulverized to obtain extract powder of hon-wasabi. 200 mg of extract powder obtained as such was filled in hard capsules (No. 3) to produce capsule food (for example, supplements, etc.) 1 mg/grain of isosaponarin is contained in the capsule.

EXAMPLE 5

Production of Food (2)

Using 150 mg of the extract powder prepared in Example 4, a raw material composition at a mixing ratio shown below was prepared and tableted to produce tablet food (for example, supplements, etc.) 0.75 mg/grain of isosaponarin is contained in the tablet.
  Tablet 1.5 g/grain (5 grains/day)
  Granulated sugar 1.20 g
  Juice concentrate 0.045 g
  Citric acid 0.075 g
  Perfume 0.03 g
  Hon-wasabi extract powder 0.15 g

EXAMPLE 6

Production of Food (3)

After 100 kg of hon-wasabi is washed and cut, 200 kg of 50% ethanol was added to obtain 180 kg of extract. The resulting extract was concentrated to remove alcohol content. After 30 kg of cellulose was added, the extract was dried and powdered. The resulting powder was tableted to produce 200 mg tablet. One tablet contains 1.0 mg of phenylpropanoid.

MODIFICATION OF EXAMPLES 4, 5, 6

In Example 5 above, an example of the tablet food was 1.5 g/grain tablet containing 0.75 mg/grain isosaponarin. The present disclosure is not limited to this. For example, 250 mg/grain tablet may contain 0.5 to 100 mg/grain isosaponarin.

Further, in Example 5, an example of a producing method of a tablet is given, but the present disclosure is not limited thereto. For example, isosaponarin and dextrin may be mixed and tableted. Further, for example, the extract powder prepared in Example 4 and dextrin may be mixed and tableted.

Further, in Example 6, although an example of the tablet containing 1.0 mg of phenylpropanoid in one tablet is given. The present disclosure is not limited thereto. For example, by changing the concentration ratio, the tablet may contain 1.0 to 100 mg of phenylpropanoid in one tablet.

EXAMPLE 7

Evaluation by Test Substance Other Than Isosaponarin

In Example 7, after culturing human hair follicle dermal papilla cells in cultures, to each of which a test substance shown in Table 1 is added, living cell count measurement, VEGF production amount, and FGF-7 gene expression level were examined.

TABLE 1

| Test Substance | Solvent | Stock Concentration |
| --- | --- | --- |
| apigenin | DMSO | 200 mmol/L |
| coumaric acid | ethanol | 200 mmol/L |
| caffeic acid methyl ester | ethanol | 200 mmol/L |

As the test materials, apigenin of catalog number 012-18913 by Wako Pure Chemical Industries, Ltd., coumaric acid of Cat. No. C9008 by Sigma-Aldrich Japan Co., Ltd., and caffeic acid methyl ester of Cat. No. J63876 by Alfa Aesar Co. were used.

Concentrations of a solvent and the stock solution used to prepare a stock solution of each test substance are also shown in Table 1. Each stock solution was sterilized by filtration for use in tests.

A 100 mmol/L stock solution of adenosine (positive control substance) was prepared using DMSO as a solvent, and added to a test medium at final concentration of 100 µmol/L (0.1% DMSO experimental section was used as a solvent control). A 15 mmol/L stock solution of minoxidil was prepared with 50% ethanol, and added to a test medium at final concentration of 30 µmol/L. Since solvent (ethanol) concentration in this case is 0.2%, 0.2% ethanol experimental section was used as the control section.

(7-1) Method of Culturing Human Hair Follicle Dermal Papilla Cells

Tested cells are human hair follicle dermal papilla cells (Cat. No. CA602t05a, Lot No. 2868, derived from parietal portion of Caucasian 51-year-old male, distributed by Toyobo Co., Ltd.). Similar to the method described in section (1-1) in Example 1, the human hair follicle dermal papilla cells were cultured.

(7-2) Toxicity Test of Human Hair Follicle Dermal Papilla Cells

Figure 6:
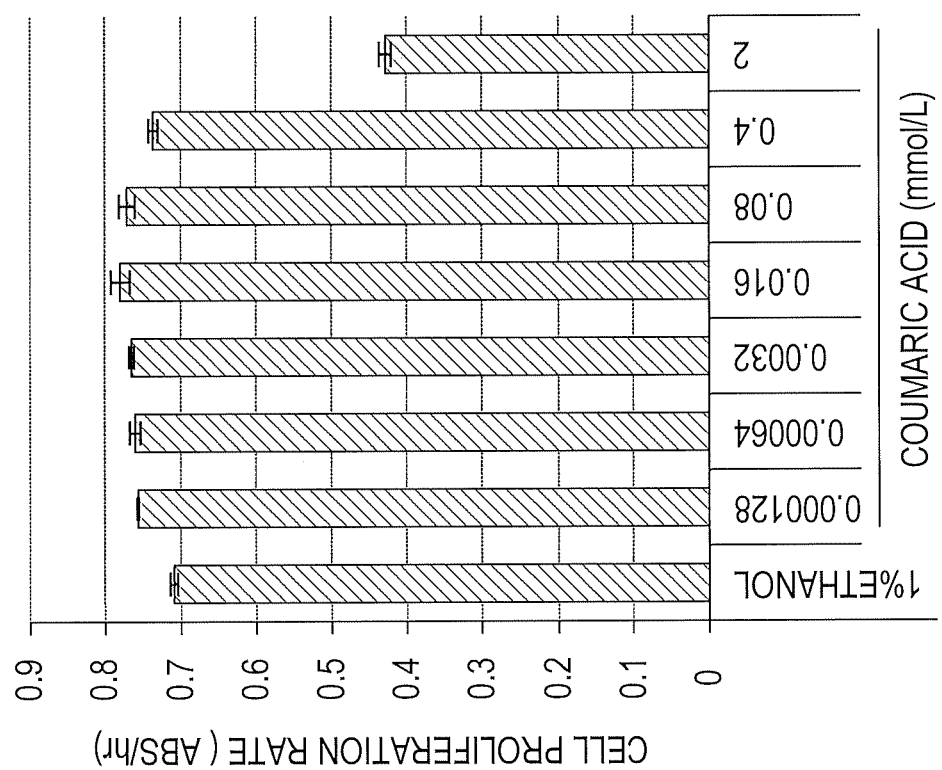
FIG. 6 is a graph showing results of a cytotoxicity test of coumaric acid using human hair follicle dermal papilla cells.
Figure 7:
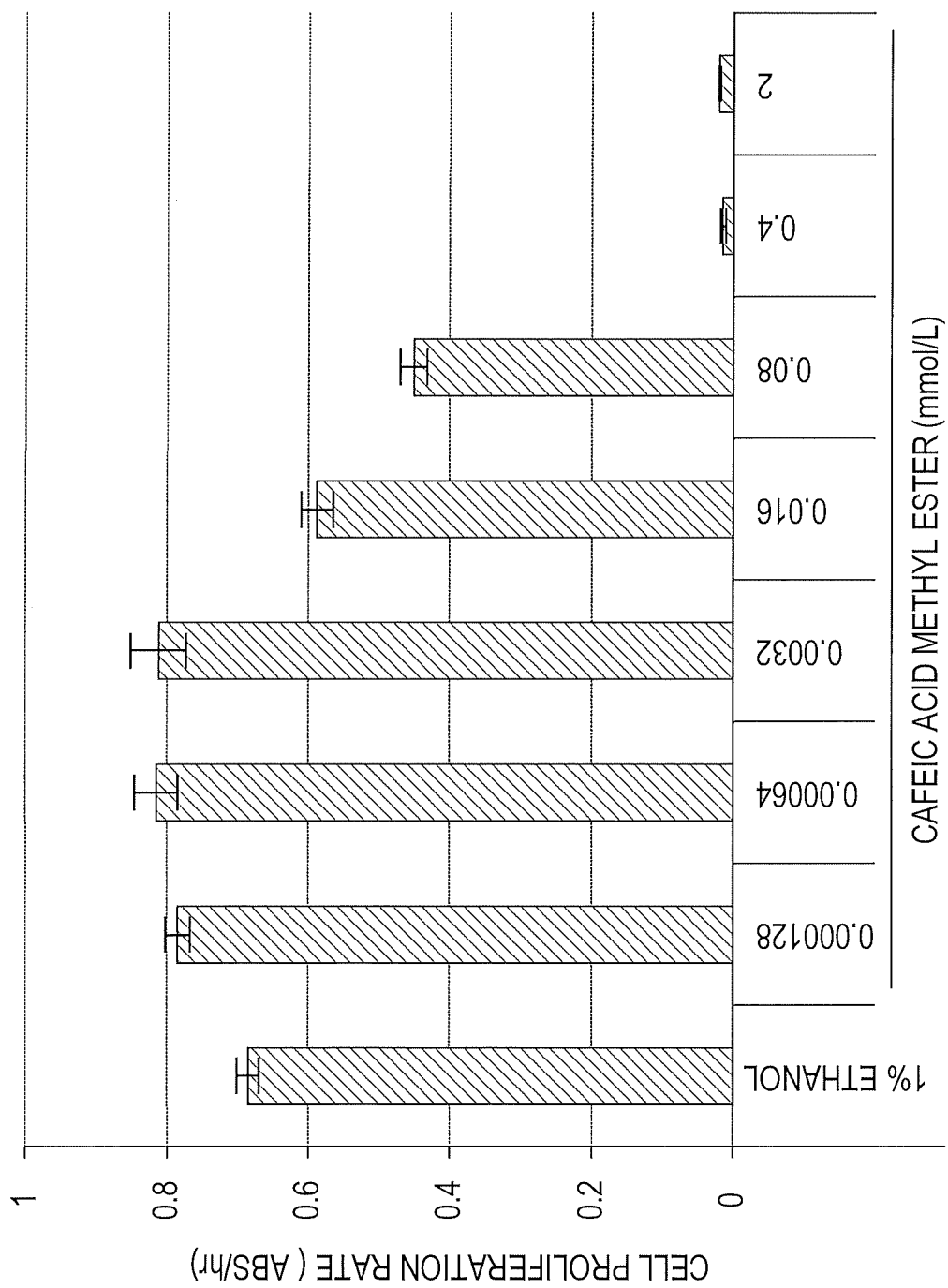
FIG. 7 is a graph showing results of a cytotoxicity test of caffeic acid methyl ester using human hair follicle dermal papilla cells.

Similar to the method described in section (1-2) in Example 1, presence or absence of toxicity to human hair follicle dermal papilla cells of the test substance was evaluated. The results are shown in FIGS. 5-7.

Figure 5:
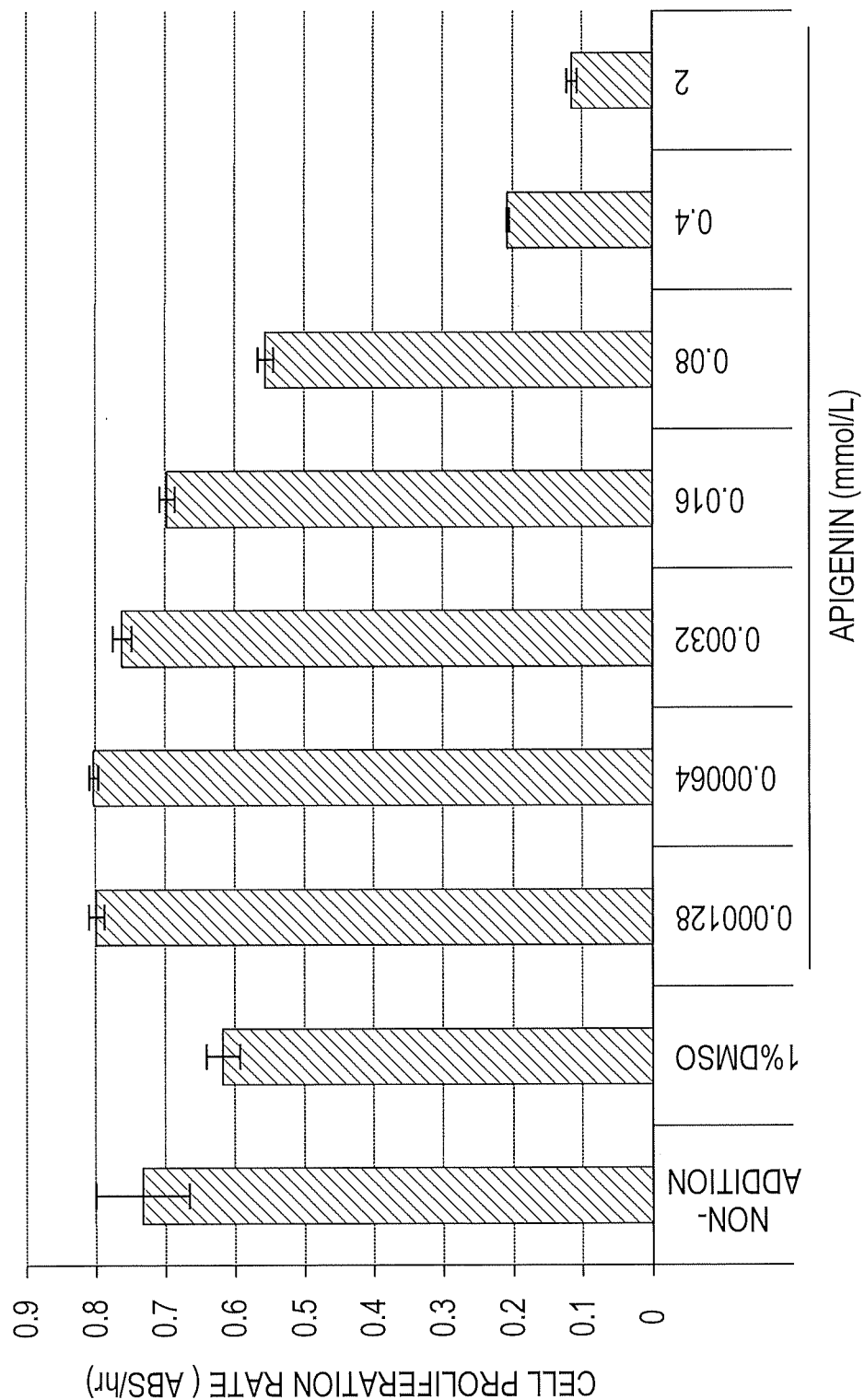
FIG. 5 is a graph showing results of a cytotoxicity test of apigenin using human hair follicle dermal papilla cells.

As shown in FIG. 5, apigenin showed toxicity to human hair follicle dermal papilla cells at 0.08 mmol/L or more. As shown in FIG. 6, coumaric acid showed toxicity to human hair follicle dermal papilla cells at 2 mmol/L or more. As shown in FIG. 7, caffeic acid methyl ester showed toxicity to human hair follicle dermal papilla cells at 0.016 mmol/L or more. Based on the results of cytotoxicity tests, the test concentrations in this test were set as shown in Table 2.

TABLE 2

| Test Substance | Solvent | Test Concentration | Solvent Concentration |
| --- | --- | --- | --- |
| apigenin | DMSO | 0.001, 0.01, 0.1, 1, 10 µmol/L | 0.005% |
| coumaric acid | ethanol | 0.001, 0.01, 0.1, 1, 10, 100 µmol/L | 0.05% |
| caffeic acid methyl ester | ethanol | 0.001, 0.01, 0.1, 1, 10 µmol/L | 0.01% |

Since the concentration of the solvent in the highest concentration of each test substance is 0.1% or less, it is determined that there is no influence of the solvent in the present test, and a non-addition control section was used as a reference in comparison of significant difference. The test was conducted as a Student T-test. It was determined that there is significance if $P<0.1$, $P<0.05$, $P<0.01$, and $P<0.001$, and the results were as shown in the figures.

(7-3) Evaluation of Human Hair Follicle Dermal Papilla Cell-Activating Action and VEGF Production Promoting Action Human hair follicle dermal papilla cells were seeded in a 48-well plate at $1.2 \times 10^4$ cells/well (0.3 mL/well in this test). After one-day culturing in a carbon dioxide incubator (5% $CO_2$, 37° C.), the cells were transferred to a medium containing the test substance. Thereafter, the cells were cultured for three days, and proliferation of each cell is compared using Living Cell Count Reagent SF. The experiment was carried out five times. After three-days culturing was completed, supernatant liquid of the culture was collected and a VEGF production amount of the supernatant was measured by ELISA kit as in Example 2.

Further, the supernatant was removed. The cells were washed with PBS, and a medium containing 10% Living Cell Count Reagent SF (300 µL/well) was then added. 100 µL per well of the culture supernatant 30 and 90 minutes after the addition was transferred to another 96-well plate and absorbance was measured with a microplate reader (measuring wavelength 450 nm, reference wavelength 595 nm). An amount of change in absorbance ABS per hour (ABS/hr) was calculated from values at 90 minutes and 30 minutes to evaluate the cell-activating action.

Figure 8:
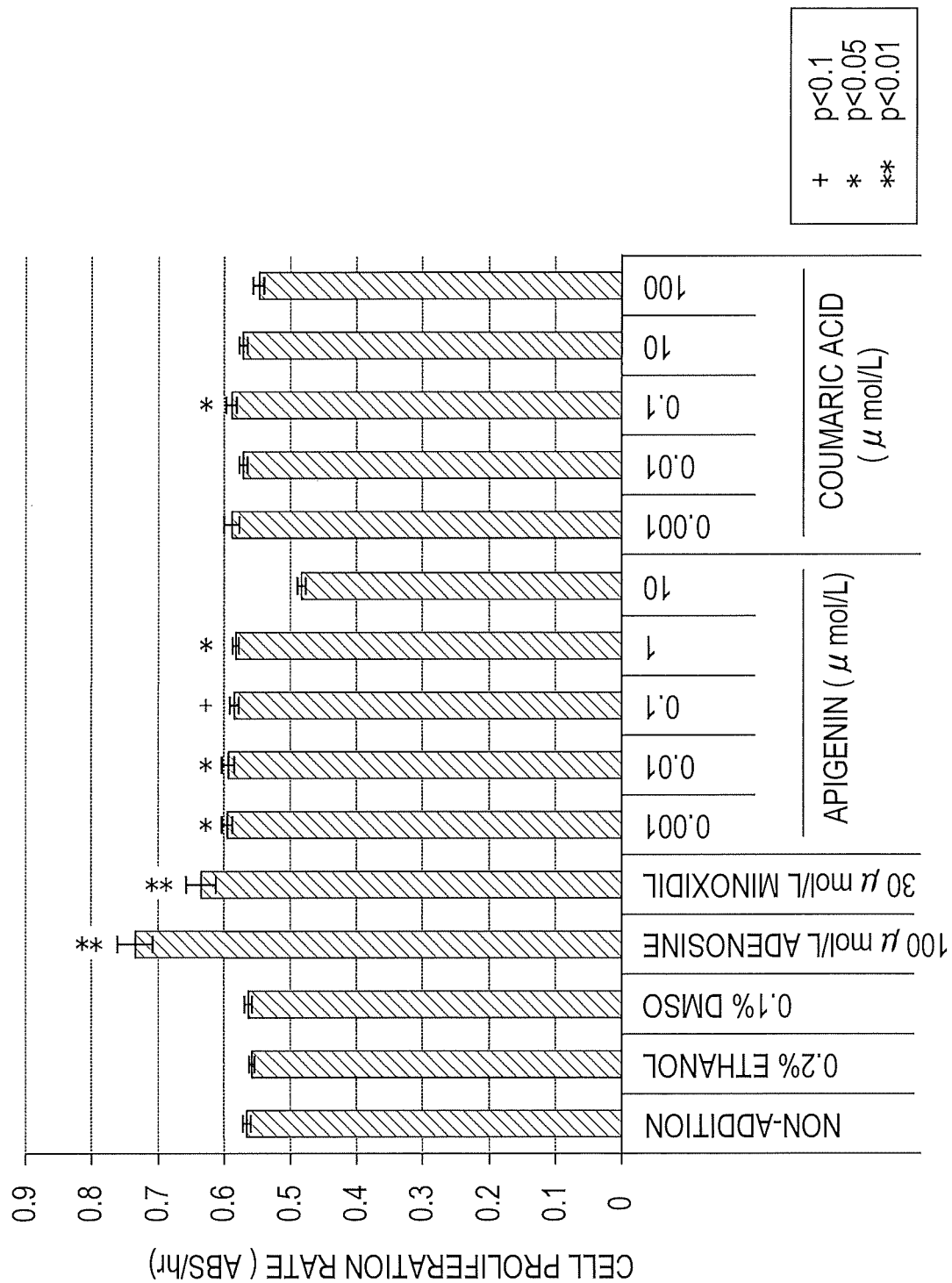
FIG. 8 is a graph showing results of studying cell-activating action by test substances other than isosaponarin using human hair follicle dermal papilla cells.
Figure 9:
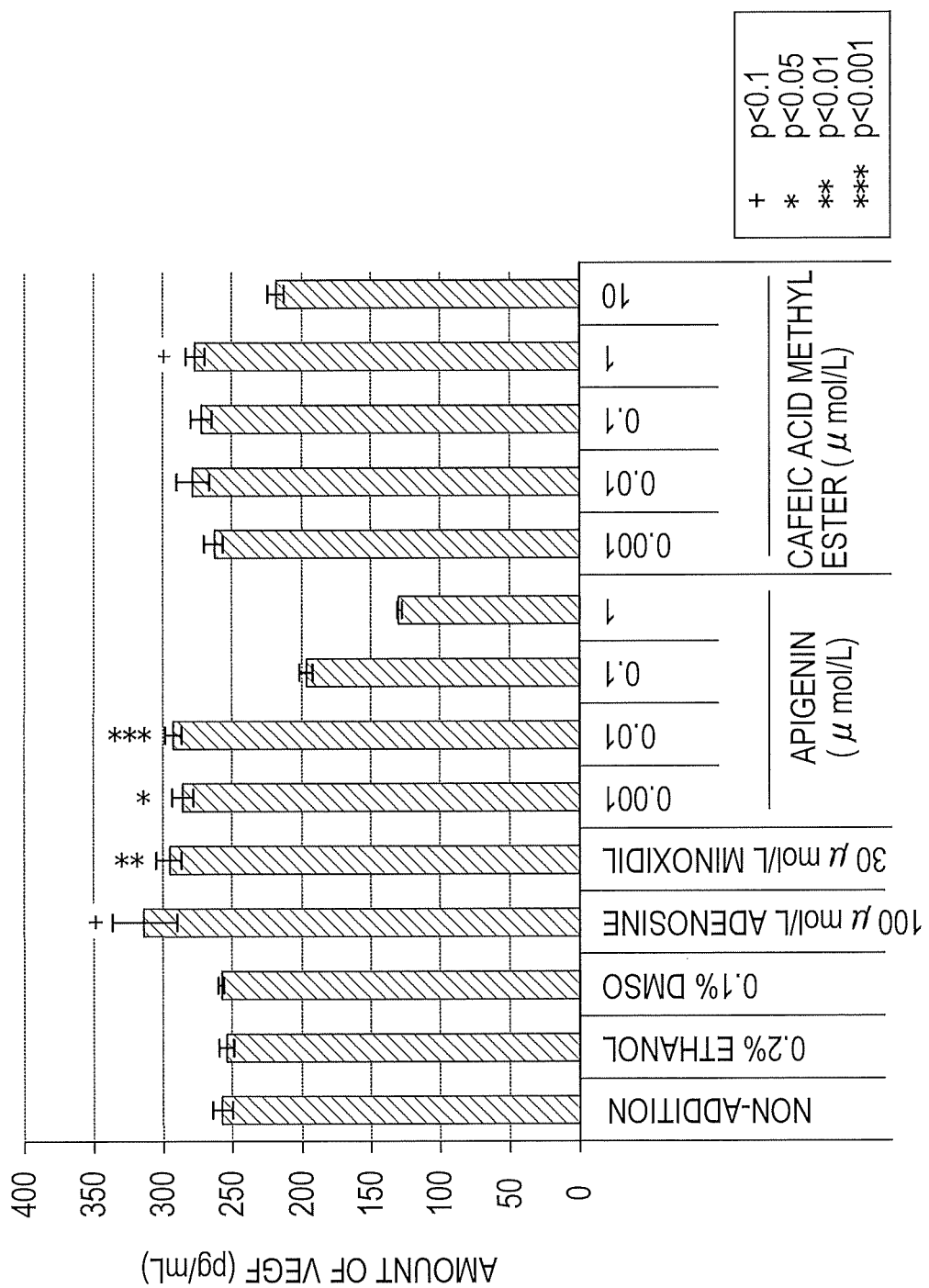
FIG. 9 is a graph showing an amount of VEGF produced by test substances other than isosaponarin using human hair follicle dermal papilla cells.

Measurement results of the number of living cells for the test substance that was determined significant by a significance test are shown in FIG. 8. FIG. 9 shows results of VEGF protein production amount.

As shown in FIG. 8, in a group treated with apigenin, more significant cell-activating action was observed on human hair follicle dermal papilla cells in the range of 0.001 µmol/L to 1 µmol/L than in the non-addition control section. Further, in the group treated with apigenin showed no significance at 10 µmol/L. Therefore, in the group treated with apigenin, it is considered that more significant cell-activating action can be observed on human hair follicle dermal papilla cells in the range of 0.001 µmol/L to 9 µmol/L than in the non-addition control section.

In a group treated with coumaric acid, more significant cell-activating action was observed on human hair follicle dermal papilla cells at 0.1 µmol/L than in the non-addition control section. Also, the group treated with coumaric acid did not show significance at 0.01 µmol/L and 10 µmol/L. Therefore, for the group treated with coumaric acid, it is considered that more significant cell-activating action can be observed on human hair follicle dermal papilla cells at 0.011 µmol/L to 9 µmol/L, preferably 0.011 µmol/L to 5 µmol/L, than in the non-addition control section.

On the other hand, more significant cell-activating action was observed on human hair follicle dermal papilla cells in adenosine (positive control substance) than in 0.1% DMSO experimental section. Further, more significant cell-activating action was observed on human hair follicle dermal papilla cells in minoxidil (positive control substance) than in 0.2% ethanol experimental section.

From the results, it is suggested that application of apigenin and coumaric acid to the scalp or the like exhibits excellent follicle dermal papilla cell-activating action, and hair restoration effect and hair growth effect can be expected.

Further, as shown in FIG. 9, in the group treated with apigenin, the amount of VEGF increased more significantly on human hair follicle dermal papilla cells in the range of 0.001 μmol/L to 0.01 μmol/L than in the non-addition control section. Further, the group treated with apigenin showed no significance at 0.1 μmol/L. Therefore, in the group treated with apigenin, it is considered that the amount of VEGF increased more significantly on human hair follicle dermal papilla cells in the range of 0.001 μmol/L to 0.09 μmol/L than in the non-addition control section.

In a group treated with caffeic acid methyl ester, an amount of VEGF increased more significantly on human hair follicle dermal papilla cells at 1 μmol/L than in the non-addition control section. Also, the group treated with caffeic acid methyl ester did not show any significance at 0.1 μmol/L and 10 μmol/L. Therefore, in the group treated with caffeic acid methyl ester, it is considered that the amount of VEGF increased more significantly on human hair follicle dermal papilla cells in a range of 0.11 μmol/L to 9 μmol/L, preferably 0.011 μmol/L to 5 μmol/L, than in the non-addition control section.

On the other hand, adenosine (positive control substance) significantly increased the amount of VEGF on human hair follicle dermal papilla cell slightly more than in 0.1% DMSO experimental section. Further, minoxidil (positive control substance) more significantly increased the amount of VEGF on human hair follicle dermal papilla cell than in 0.2% ethanol experimental section.

(7-4) Evaluation of FGF-7 Gene Expression

Human hair follicle dermal papilla cells were seeded in a collagen-coated 48-well plate at $1 \times 10^5$ cells/well (0.3 mL/well in this test). After one-day culturing (confirm 100% confluent) in the carbon dioxide incubator (5% $CO_2$, 37° C.), the cells were transferred to a medium containing the test substance (3-step concentration: non-toxic concentration range). Then, the cells are cultured for two hours, and total RNA was recovered and reverse transcribed into cDNA. Thereafter, FGF-7 gene expression was measured by real-time PCR. Using GAPDH gene as an internal reference, FGF-7 gene expression was calculated as a relative value of the negative control section. The experiment was carried out three times. Details of each procedure are shown below.

First, collection of total RNA from the cells and cDNA synthesis were carried out according to the steps of FastLane Cell RT-PCR kit.

Step 7-1. 500 μL per well of buffer FCW was added to the cells washed with PBS, and the buffer FCW was immediately removed and aspirated.

Step 7-2. 200 μL per well of the buffer FCP was added. After incubation for 5 minutes at room temperature (25° C.), FastLane lysate was transferred to a 96-well PCR tube. The tube was stored at −80° C. until the next cDNA synthesis.

Step 7-3. Lysate in Step 7-2 was dissolved at room temperature. 2 μL of gDNA Wipeout Buffer, 1μL of FastLane lysate and 11 μL of RNase-free water were added to a new PCR tube, caused to react for 5 minutes at 42° C., and then transferred immediately to ice. (In fact, an appropriate amount of master mix of gDNA Wipeout Buffer and RNase-free water was added to the tube containing lysate.)

Step 7-4. 6 μL of the reverse transcription reaction master mix was added to 14 μL of reaction solution obtained in Step 7-3 and incubated for 30 minutes at 42° C. (1 μL of Quantiscript Reverse Transcriptase, 4 μL of Quantiscript RT Buffer, 1 μL of RT Primer Mix/tube).

Step 7-5. The reaction solution was treated for 3 minutes at 95° C., to inactivate the reverse transcriptase. This reaction solution was used for real-time PCR as a synthetic cDNA. The reaction solution was stored at −80° C. until used in analysis.

Next, the reaction solution was adjusted as follows in a real-time PCR dedicated tube, and PCR was carried out. PCR was carried out for 60 cycles at 95° C. for 10 seconds and 60° C. for 30 seconds.

| | |
|---|---|
| $dsH_2O$ | 2.4 μL |
| SYBER Premix Ex Taq | 4.0 μL |
| forward primer (20 μmol/L) | 0.3 μL |
| reverse primer (20 μmol/L) | 0.3 μL |
| synthesized cDNA | 1.0 μL |
| total | 8.0 μL |

Specific primers of FGF-7 used in the test and specific primers of GADPH used as an internal reference are shown below.

```
Primers of FGF-7
forward primer:
                                    (SEQ ID NO: 1)
tctgtcgaacacagtggtacctgag reverse primer:
                                    (SEQ ID NO: 2)
gccactgtcctgatttccatga Primers of GADPH
forward primer:
                                    (SEQ ID NO: 3)
catccctgcctctactggcgctgcc reverse primer:
                                    (SEQ ID NO: 4)
ccaggatgcccttgaggggccctc
```

The relative expression level of each gene was calculated as follows. From an intersection of an amplification curve of each gene and a threshold line of each gene, a Ct value (the number of PCR cycles) was calculated. ΔCt value is obtained by subtracting a Ct value of the internal reference GAPDH gene from a Ct value of the target gene (Ct values (target gene)−Ct (GAPDH2)=ΔCt value). Further, ΔΔCt value is obtained by subtracting an average ΔCt value of a blank from ΔCt value (ΔCt value (sample treatment section)−ΔCt (blank section)=ΔΔCt value). A relative expression level is $2^{-\Delta\Delta CT}$ value obtained by substituting the ΔΔCt value into a multiplier term.

Figure 10:
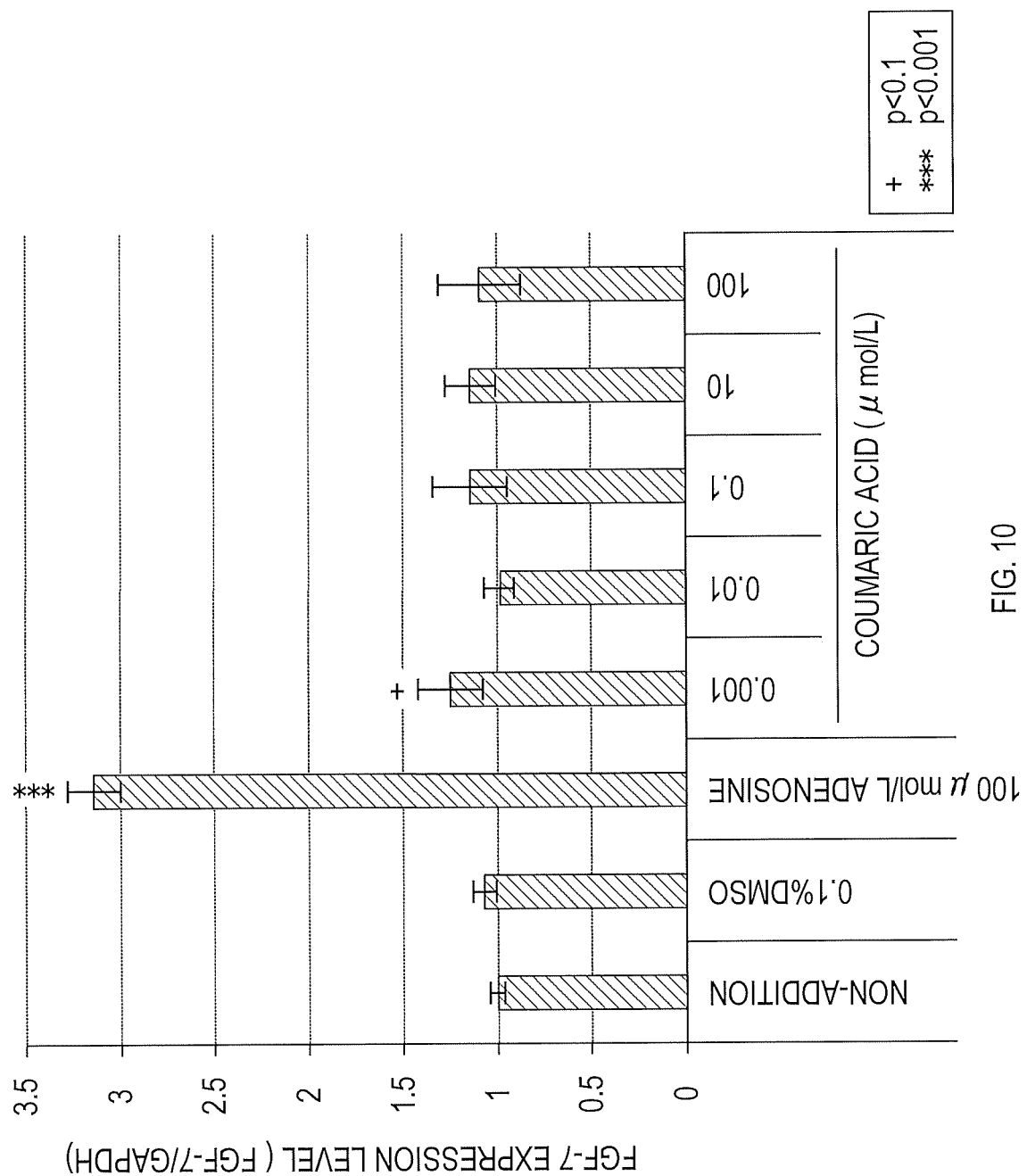
FIG. 10 is a graph showing expression level of FGF-7 gene by test substances other than isosaponarin using human hair follicle dermal papilla cells.

FIG. 10 shows results of the FGF-7 gene expression level for the test substance determined significant by the significance test.

As shown in FIG. 10, in the group treated with coumaric acid, FGF-7 gene expression was more significantly elevated in human hair follicle dermal papilla cells at 0.001 μmol/L, than in the non-addition control section. Also, the group treated with coumaric acid did not show any significance at 0.01 μmol/L. Therefore, for the group treated with coumaric acid, it is considered that elevated FGF-7 gene expression will be more significantly exhibited at 0.001 μmol/L to 0.009 μmol/L, preferably 0.001 μmol/L to 0.005 μmol/L on human hair follicle dermal papilla cells, than in the non-addition control section.

On the other hand, adenosine (positive control substance) showed more significantly elevated FGF-7 gene expression on human hair follicle dermal papilla cells than in 0.1% DMSO experimental section.

Examples of the hair restoration/growth stimulating agent have been described above. The example configurations in the above Examples can be variously modified. For example, in the above Examples, the example flavonoids represented by the formula (I) are isosaponarin and apigenin, but they are not limited thereto. Besides isosaponarin and apigenin, the example flavonoids already shown herein can be used. Even with these flavonoids, the same hair restoration/growth stimulating effect as in the case of using isosaponarin can be expected.

Further, hon-wasabi is used as an example raw material for cosmetics and foods in the above Examples. However, the raw material for cosmetics and food is not limited thereto, and may be a horseradish, or may be used in combination with hon-wasabi and horseradish, for example.

[Sequence Listing]

The invention claimed is:

1. A method of promoting activation of follicle dermal papilla cells of a subject, the method comprising;
   administrating a follicle dermal papilla cell activation promoting agent to the subject,
   wherein the follicle dermal papilla cell activation promoting agent comprises at least one of flavonoid, excluding apigenin or luteolin, represented by a formula (I) below as an active ingredient:

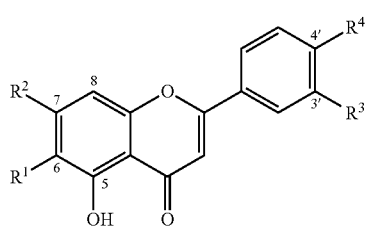

where $R^1$ is a glycosyl, glycosyl-glycosyl-O-sinapoyl or H, $R^2$ is O-sinapoyl or OH, $R^3$ is H or OH, $R^4$ is O-glycosyl, OH or O-glycosylation-sinapoyl.

2. The method of promoting activation of follicle dermal papilla cells according to claim 1, wherein the flavonoid includes isosaponarin.

3. The method of promoting activation of follicle dermal papilla cells according to claim 1, wherein administrating of the follicle dermal papilla cell activation promoting agent is oral ingestion of the follicle dermal papilla cell activation promoting agent.

4. The method of promoting activation of follicle dermal papilla cells according to claim 1, wherein administrating of the follicle dermal papilla cell activation promoting agent is application of the follicle dermal papilla cell activation promoting agent to a scalp.

5. The method of promoting activation of follicle dermal papilla cells according to claim 1, wherein the follicle dermal papilla cell activation promoting agent is administrated in one form selected from a group consisting of ampoule, capsule, powder, granule, pill, tablet, solid, liquid, gel, bubble, milky lotion, cream, ointment, sheet, and mousse.

6. The method of promoting activation of follicle dermal papilla cells according to claim 1, wherein the flavonoid is an ingredient extracted from at least one of wasabi or horseradish.

7. A method of promoting production of a vascular endothelial growth factor (VEGF) in follicle dermal papilla cells of a subject, the method comprising
   administrating a VEGF production promoting agent for the follicle dermal papilla cells to the subject,
   wherein the VEGF production promoting agent comprises at least one of flavonoid, excluding apigenin or luteolin, represented by a formula (I) below as an active ingredient:

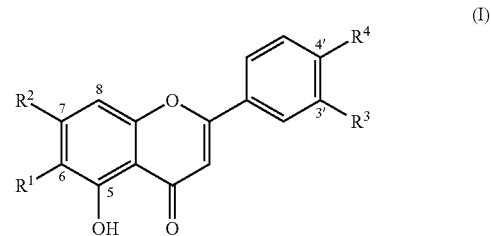

where $R^1$ is a glycosyl, glycosyl-glycosyl-O-sinapoyl or H, $R^2$ is O-sinapoyl or OH, $R^3$ is H or OH, $R^4$ is O-glycosyl, OH or O-glycosylation-sinapoyl.

8. The method of promoting the VEGF according to claim 7, wherein the flavonoid includes isosaponarin.

9. The method of promoting the VEGF according to claim 7, wherein administrating of the VEGF production promoting agent is oral ingestion of the VEGF production promoting agent.

10. The method of promoting the VEGF according to claim 7, wherein administrating of the VEGF production promoting agent is an application of the VEGF production promoting agent to a scalp.

11. The method of promoting the VEGF according to claim 7, wherein the VEGF production promoting agent is administrated in one form selected from a group consisting of ampoule, capsule, powder, granule, pill, tablet, solid, liquid, gel, bubble, milky lotion, cream, ointment, sheet, and mousse.

12. The method of promoting the VEGF according to claim 7, wherein the flavonoid is an ingredient extracted from at least one of wasabi or horseradish.

13. A method of stimulating hair restoration/growth of a subject, the method comprising
   administrating a hair restoration/growth stimulating agent to the subject,
   wherein the hair restoration/growth stimulating agent comprises at least one of flavonoid, excluding apigenin or luteolin, represented by a formula (I) below as an active ingredient:

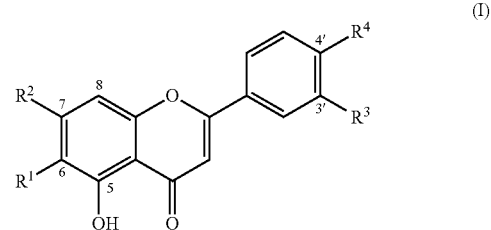

where $R^1$ is a glycosyl, glycosyl-glycosyl-O-sinapoyl or H, $R^2$ is O-sinapoyl or OH, $R^3$ is H or OH, $R^4$ is O-glycosyl, OH or O-glycosylation-sinapoyl.

14. The method of stimulating hair restoration/growth according to claim 13, wherein the flavonoid includes isosaponarin.

15. The method of stimulating hair restoration/growth according to claim 13, wherein administrating of the hair restoration/growth stimulating agent is oral ingestion of the hair restoration/growth stimulating agent.

16. The method of stimulating hair restoration/growth according to claim 13,
wherein administrating of the hair restoration/growth stimulating agent is application of the hair restoration/growth stimulating agent to a scalp.

17. The method of stimulating hair restoration/growth according to claim 13,
wherein the hair restoration/growth stimulating agent is administrated in one form selected from a group consisting of ampoule, capsule, powder, granule, pill, tablet, solid, liquid, gel, bubble, milky lotion, cream, ointment, sheet, and mousse.

18. The method of stimulating hair restoration/growth according to claim 13,
wherein the flavonoid is an ingredient extracted from at least one of wasabi or horseradish.

* * * * *